Feb. 21, 1967 L. E. GAVELLO Plant Pat. 2,720
HEBE (VERONICA) PLANT
Filed Oct. 21, 1965
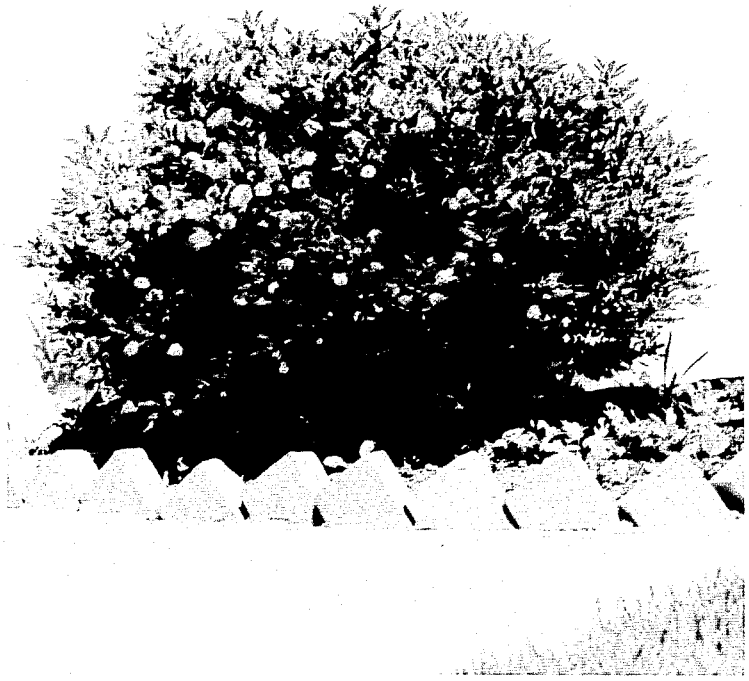
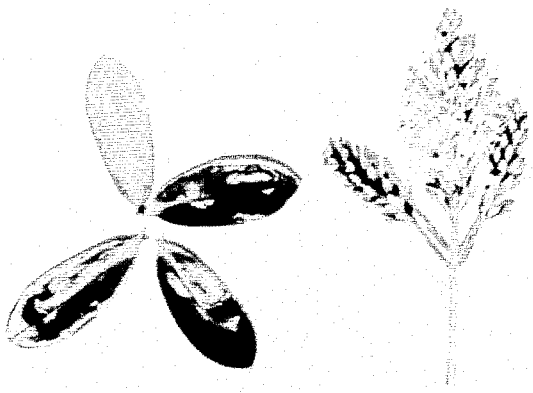
Inventor: LOUIS E. GAVELLO
By
Warren, Brosler, Cypher + Anglim
Attorneys United States Patent Office Plant Pat. 2,720
Patented Feb. 21, 1967

2,720
HEBE (VERONICA) PLANT
Louis E. Gavello, 3436 Maricopa Ave.,
Richmond, Calif. 94804
Filed Oct. 21, 1965, Ser. No. 500,459
1 Claim. (Cl. Plt.—54)

My invention relates to a new and distinct variety of Hebe (Veronica) plant, originating as a cultivated seedling of the variety Hebe hybrid "Veronica Coed," Plant Patent No. 2,296. Seeds taken from "Veronica Coed" in 1961 were planted in my nursery located in Richmond, California. The distinctive characteristics of this particular seedling were observed by me at the time of its initial blooming and the first asexual reproduction by cuttings therefrom was made by me at my nursery in Richmond, California in 1963. Approximately 500 asexual reproductions have been made and cuttings are now being taken from the second generation.

Among the outstanding characteristics of the new variety, the following features contribute to the novelty and distinctiveness thereof, and represent a unique combination which is definitely different from that found in my variety "Veronica Coed," or in any other variety of Hebe plant of which I am aware:

(1) Bush is of a low height, compact, round, of wide spread and of rapid growth;

(2) Branches are substantially straight with leaves sessile and opposed to each other in pairs, with the pairs of leaves spaced alternately along the branch 180 degrees apart.

(3) Blooms are profuse, there being many racemes at the end of each branch; the florets on racemes opening initially from base to tip, are of a lavender color as they open and changing to white progressively from base to tip; the buds being white-tipped and turning from white to lavender to open into the lavender florets.

The accompanying drawing shows, in separate views, a typical bush of my new variety of Hebe plant, specimens of individual leaves and a number of racemes on a branch in different stages of development and as depicted in color as nearly true as it is reasonably possible to make the same in a color illustration of this character.

The following is a detailed description of the new variety, with color terminology in accordance with Maerz and Paul, A Dictionary of Color, 2nd edition, 1950.

Parentage: Seedling of Hebe hybrid, "Veronica Coed," Plant Patent No. 2,296.

Classification: Botanic—Hebe (Veronica).

*Plant*

Form: Bush—approximately 25 inches tall with an approximately 36 inch spread; round; compact; vigorous.

Rate of growth: Grew approximately 25 inches in 2 years.

Time to maturity: Approximately 3 years.

Branches: Length may vary up to approximately 25 inches. Color—Cordovan (Woodland Brown), Plate 8—H-8.

Foliage:

*Leaves.*—Evergreen; glabrous only on upper side; smooth; thick; elliptic obovate, narrowing toward base; sessile.

*Length of leaves.*—1 to 1¼ inches.

*Width of leaves.*—½ to ⅝ inch at widest portion.

*Rib.*—Prominent mid rib on reverse side from base to tip.

*Leaf arrangement.*—Opposite in pairs; alternately 180 degrees apart, with pairs spaced from each other along branch at their jointure thereto approximately ¼ inch apart.

*Color.*—Upper side, Plate 23—L-11. Reverse side, Plate 21—G-5.

Flower:

*Blooms.*—Latter part of May and September in Richmond, California.

*Racemes.*—Single on a peduncle; compact, axillary compound; conical. Length—in flower, approximately 1 to 1¼ inches. Width at base—in flower, approximately ½ to ¾ inch. Number—approximately 10 to 12 at the end of each branch. Buds—Green, Plate 21—G-1, becoming white-tipped turning to lavender and opening to lavender floret. Florets—stalked on peduncle; initially of a general lavender color ranging from Plate 42—C-3, 4, 5 to Plate 43—C-5, 6 and predominantly Lavender, Plate 43—C-5; changing to white progressively from base to tip of raceme. Number—approximately 40 florets to each raceme. Filaments and anthers—two stamens and a stigma in each floret extending approximately ¼ inch beyond the floret; color of anthers, Plate 42—L-10.

Weather resistance: Exposure to sun—good. Exposure to wind—good.

Disease resistance: Resistant to blight and fungus diseases and most others.

Having described and illustrated my new variety of Hebe (Veronica) plant, I claim:

A new and distinct variety of Hebe (Veronica) plant, substantially as illustrated and described, characterized as to novelty by:

(a) the compact, rounded form of the plant having a low height and a spread greater than its height, (b) the paired, spaced arrangement of the leaves on its long branches, alternately disposed 180 degrees apart, the leaves being sessile, (c) the profuse grouping of conical shaped compound racemes, each on a separate peduncle at the end of each branch, (d) the buds being white-tipped and changing to a lavender color and opening to lavender color florets, (e) the florets changing from their initial lavender color to white, progressively from base to tip of raceme, (f) the dark green color of its leaves, effectively contrasting with the lavender color of its flowers, and then the white color thereof as they change from lavender to white, (g) its resistance to weather and disease, and (h) its rapid growth and suitability for garden decorative purposes over a blooming season in early summer and fall.

No references cited.

ABRAHAM G. STONE, *Primary Examiner.*

R. E. BAGWILL, *Assistant Examiner.*